United States Patent [19]

Roline et al.

[11] 4,363,325

[45] Dec. 14, 1982

[54] MODE ADAPTIVE PACER

[75] Inventors: Glenn Roline, Anoka; Frank Walmsley, New Brighton, both of Minn.

[73] Assignee: Medtronic, Inc., Minneapolis, Minn.

[21] Appl. No.: 226,304

[22] Filed: Jan. 19, 1981

[51] Int. Cl.³ ............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,557,796 | 1/1971 | Keller, Jr. et al. | 128/419 PG |
| 3,648,707 | 3/1972 | Greatbatch | 128/419 P |
| 3,661,157 | 3/1972 | Fyson et al. | 128/419 PG |
| 4,059,116 | 11/1977 | Adams | 128/419 PG |
| 4,248,238 | 2/1981 | Joseph | 128/419 PG |

OTHER PUBLICATIONS

Technical Manual for Model 2409 Programmable Atrial Synchronous Ventricular Inhibited Pulse Generator, Mar., 1981; Issued by Medtronic, Inc.

Primary Examiner—William E. Kamm
Attorney, Agent, or Firm—Robert C. Beck; John L. Rooney; Joseph F. Breimayer

[57] ABSTRACT

A multiple-mode pacer which automatically switches from an atrial synchronous mode to a ventricular inhibited mode when the intrinsic atrial rate drops below a preset hysteresis rate. This mode switching prevents atrial bradycardia from resulting in the delivery of closely spaced ventricular stimulating pulses.

4 Claims, 2 Drawing Figures

MODE ADAPTIVE PACER

BACKGROUND OF THE INVENTION

1. Field of the Invention

This invention relates to a multiple-mode pacer and more specifically, to a pacer which switches from atrial synchronous to a ventricular inhibited mode when the detected intrinsic atrial rate drops below a specified hysteresis rate.

2. Description of the Prior Art

Atrial synchronous pacing is a desirable pacing mode since it most nearly approximates the normal physiological mechanism of the heart. However, such pacers (VDD, DDD, VAT) have not been widely accepted because of the undesirable interaction between the heart and the pacer at the upper and lower rates.

The pacer of the present invention is directed toward a problem exhibited by prior art pacemakers when the detected atrial rate is low. This problem will be described after a discussion of the operation of a normal heart and a brief review of two of the predominate prior art atrial synchronous pacing modes.

In the normal heart the upper chambers or atria contract in a separate action which precedes the contraction of the lower chambers or ventricles. Although the contribution of the atrial contraction is not necessary to sustain life, it does improve the efficiency of the ventricular contraction or systole and aids in the operation of the heart valves. This contraction sequence is normally initiated by electrical activity originating in the sino-atrial (S-A) node. This stimulus is propagated throughout the atrium which contracts. Subsequently, the stimulus is conducted to the atrio-ventricular (A-V) node which delays the delivery of the stimulus to the ventricles for a brief period of time. This (A-V) delay in the heart's conduction system results in the proper temporal relation between the atrial and ventricular contractions of the cardiac cycle.

The electrical activity originating from the cardiac cycle may be recorded at the surface of the body on an electrocardiogram (EKG) which displays a repetitive waveform exhibiting P, Q, R, S, and T wave segments. The P-wave results from the atrial contraction and it is followed by the QRS complex or R-wave portion of the waveform resulting from the ventricular contraction. The time period from the P-wave to the R-wave displayed on the EKG indicates the duration of the A-V delay of the patient's natural conduction system. The T-wave following the R-wave indicates the repolarization or return of the ventricles to the resting state. During this T-wave segment, the heart is particularly vulnerable to life-threatening ventricular fibrillation induced by a pacing stimulus delivered to the ventricle during this T-wave portion of the cardiac cycle. In the normal heart the cardiac cycle repeats at a frequency between 50 and 100 times per minute. On the EKG the heart rate is measured on a beat-to-beat basis by noting the time interval between successive R-waves. For example, the normal resting heart rate of 70 bpm corresponds to an R to R interval of 857 milliseconds.

Atrial synchronous pacers of the VDD and DDD type are indicated for those patients who exhibit reliable intrinsic activity but who have lost A-V synchrony due to a conduction disturbance which interferes with the normal A-V conduction paths. The degree of this atrio-ventricular block indicates the type of atrial synchronous pacer which must be prescribed. The principal atrial synchronous pacing modes include the VAT or atrial synchronous pacer and the VDD or atrial synchronous ventricular inhibited pacer.

A VAT pacer senses the P-wave of the atrium and triggers a ventricular stimulting pulse after an appropriate A-V delay. This delay mimics the normal A-V delay of the heart and restores the proper A-V synchrony between the chambers of the heart.

A VDD pacer senses both P-waves from the atrium and R-waves from the ventricles. In operation, the detected P-wave triggers a ventricular stimulating pulse after an appropriate A-V delay unless the ventricular sense amplifier detects a ventricular contraction during this time period.

Consequently, both of these pacers synchronize the stimulated ventricular event with the intrinsic atrial event which increases cardiac output in some patients and also permits the pacer to follow or track the physiologically determined atrial rate to mimic the natural activity of the normal heart. Thus far these two pacing modalities have been described with respect to the events of a single cardiac cycle.

The VDD pacer, unlike the VAT pacer, provides an inhibit demand pacing function of the ventricles. For example, if ventricular activity occurs during the escape interval, the pacer will not pace in the ventricle until another escape interval expires. At low atrial rates the VDD and VAT pacers revert to a fixed asynchronous ventricular pacing rate.

This stimulation regime can, under certain circumstances, result in the delivery of two closely spaced ventricular stimulating pulses. This is undesirable since the second of these pulses may occur during the vulnerable period of the T-wave at the higher rates. This phenomena may occur if no P-wave is detected during the ventricular escape interval. The absence of this P-wave will result in the asynchronous stimulation of the ventricle. However, if the atria contracts just after the ventricle has been stimulated, then the resultant P-wave will be detected by the pacer; and the pacer will resynchronize on it and deliver another output pulse to the ventricle. These two ventricular stimulating pulses will be separated by a time period corresponding to the upper rate limit characteristic of the pacer.

The prior art teaches two solutions to this problem. The first of these is to increase the A-V delay of the pacemaker such that the second of the two stimulating pulses will not fall within the T-wave. This solution is unsatisfactory since this exaggerated A-V delay reduces the effective pumping efficiency of the heart.

A second prior art solution to this problem is to provide a long refractory period for the atrial sense amplifier. This technique prevents the atrial sense amplifier from sensing atrial activity until a preset delay beyond the delivery of the last stimulating pulse. Although this excessively long refractory period ensures that the pacer will not detect a conducted P-wave, it is undesirable since it may result in missed detection of normal sinus rhythm at high intrinsic rates.

SUMMARY OF THE INVENTION

The pacer, according to the present invention, addresses this problem and assures that atrial bradycardia will not result in the stimulation of the ventricle twice in quick succession.

This result is achieved by mode switching, which causes the pacer to leave an atrial synchronous (VDD)

mode and enter a ventricular inhibited mode (VVI) if no atrial activity is sensed within a preset escape interval referred to as the hysteresis period. Return from the VVI mode to the VDD mode is accomplished in response to a detected intrinsic atrial rate which is higher than a preset ventricular (lower) rate.

DETAILED DESCRIPTION OF THE PREFERRED EMBODIMENT

The pacer of the present invention is capable of operating in the ventricular demand mode (VVI) and the atrial synchronous ventricular inhibited mode (VDD). The pacer will automatically switch from the VDD mode to the VVI mode at a preset atrial rate referred to as the hysteresis rate. The pacer will return from the VVI mode to the VDD mode at a detected atrial rate referred to as the lower escape rate.

The therapeutic objective of mode switching is to prevent detected atrial bradycardia from resulting in closely spaced ventricular stimulating pulses.

Figure 1:
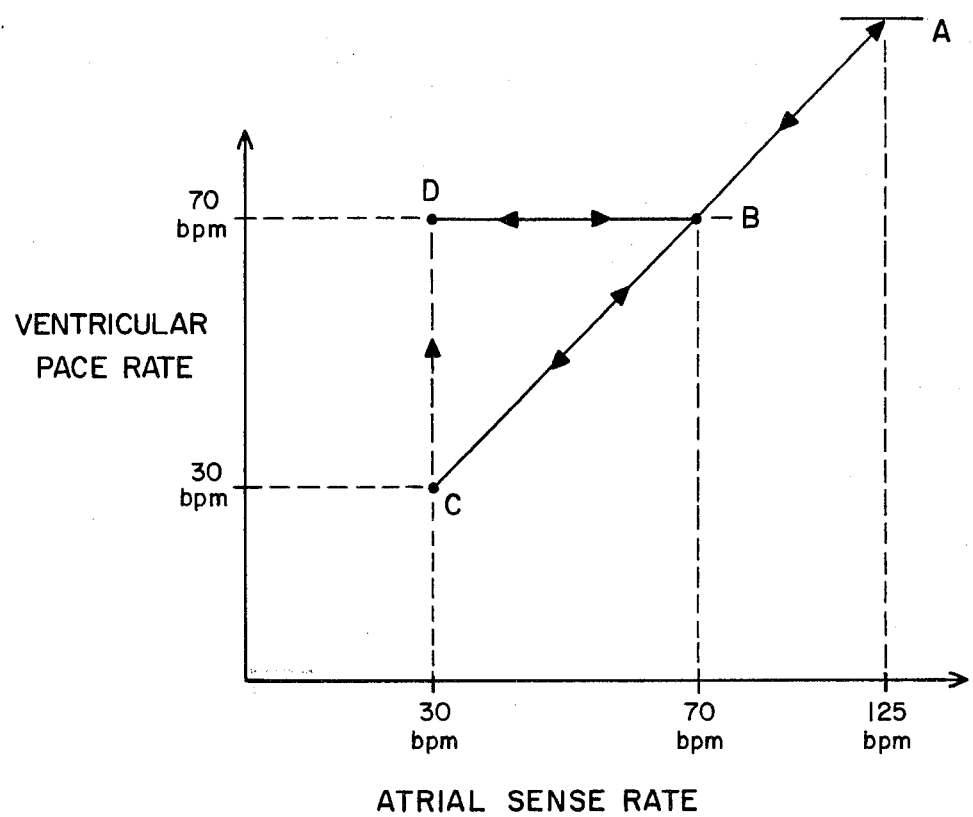
FIG. 1 is a hysteresis diagram illustrating the modes of operation of the pacemaker of the present invention.

The operational objective of the mode switching pacer is most easily understood with reference to the hysteresis diagram of FIG. 1, which shows the detected atrial rate on the abscissa and the ventricular stimulus output rate on the ordinate. The diagonal segment AC corresponds to operation in the VDD mode while horizontal segment DB corresponds to operation of the pacer in the VVI mode.

The mode switching atrial rates are shown by point C and point D. The pacer, during normal operation, will be confined to the VDD mode corresponding to segment AC. If, however, the detected atrial rate drops below the 30 bpm hysteresis indicated by point C, then the pacemaker will switch to the VVI mode. This mode switching is indicated by line segment CD on the diagram. During this mode of operation the pacer will operate in the VVI mode corresponding to segment DB. If the detected atrial rate rises above the point B rate, then the pacer will switch back to the VDD mode.

In summary, the pacer will operate in the VDD mode unless the detected atrial rate of the patient drops below approximately 30 bpm. At this point the pacer will switch to the VVI mode and operate in this pacing regime until the patient's atrial rate exceeds approximately 70 bpm.

It is anticipated that the mode switching rates will be programmable and will be selected by the physician for the individual patient. Typically, the objective of this programming will be to confine the pacer to the VDD mode except during extraordinary circumstances.

Figure 2:
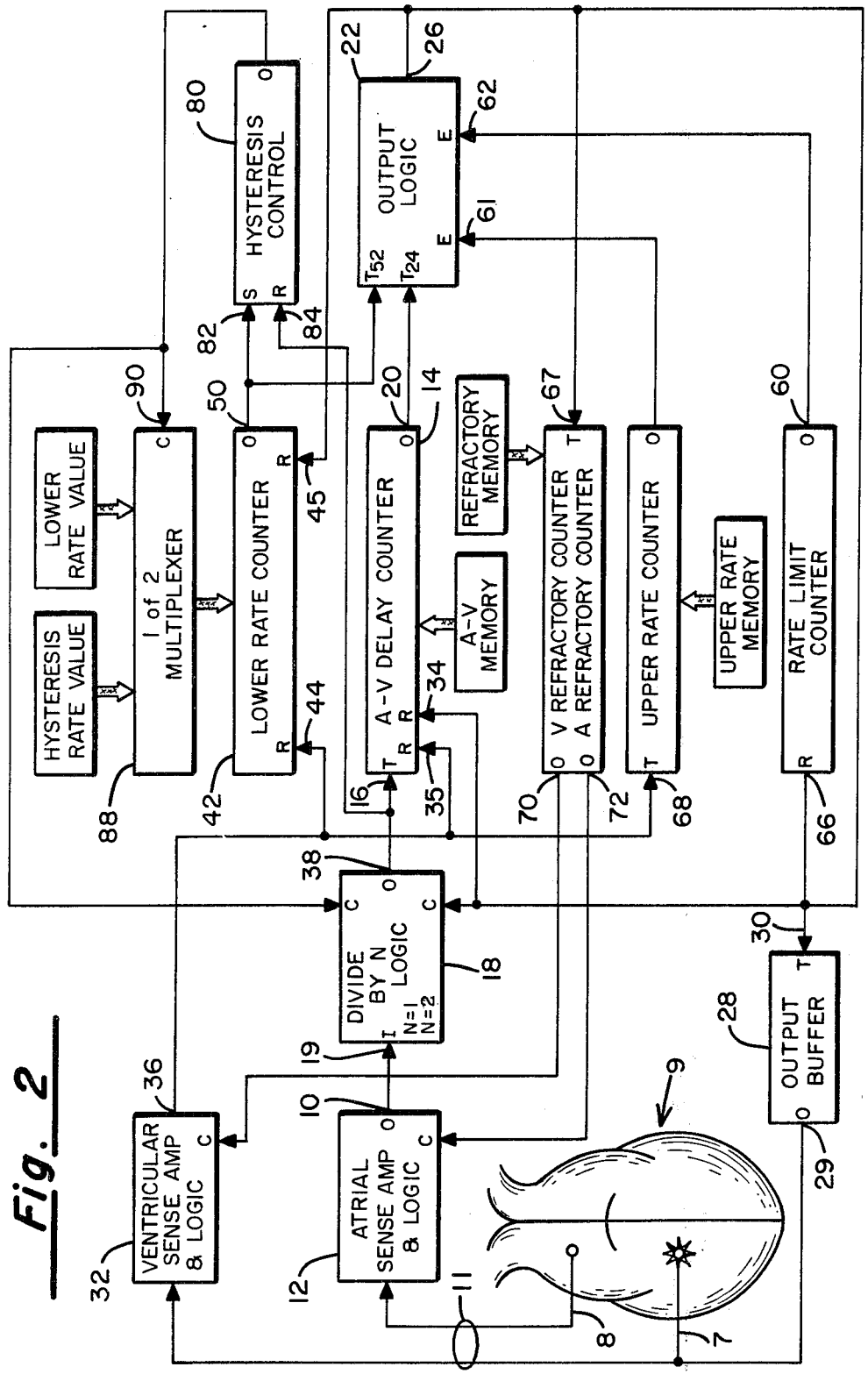
FIG. 2 is a functional block diagram suitable to produce a hardware implementation of the present invention.

The block diagram of FIG. 2 shows one collection of functional elements which may be used to implement the present invention.

The specific operation of the functional block shown in FIG. 2 is most easily understood by considering the VDD and VVI operations separately and then discussing the various control signals which cooperate to switch the pacer operation between these two modes. In the contemplated embodiment, various features of the pacer are remotely programmable such as lower rate, hysteresis rate and atrio-ventricular delay interval. This is shown on the diagram by blocks of programmable memory associated with the respective counters of the pacer.

Beginning with the atrial synchronous ventricular inhibited mode (VDD) it is important to recall that the pacer must sense naturally occurring electrical activity in both the atrium and the ventricle and provide ventricular stimulating pulses only in the absence of naturally occurring or normally conducting ventricular beats. Consequently, the patient's heart 9 is coupled to the pacer through a lead interface 11 having an atrial conductor 8 and a ventricular conductor 7. The atrial sense amplifier 12 is coupled to the atrium through conductor 8 and produces a logic level output at output 10 when an atrial depolarization is detected. Likewise, the ventricle is connected to the ventricular sense amplifier 32 through conductor 7. The sense amplifier detects ventricular depolarizations and produces a logic level output indicative of this event at its output 36. In a similar fashion, output stimulii from output buffer 28 are communicated to the ventricle from the output 29 of the buffer through the conductor 7 to the ventricle.

In the VDD mode of operation, sensed atrial activity will start a delay counter which will initiate a ventricular stimulus unless the delay counter is reset by a detected ventricular depolarization. In the diagram the atrial sensed amplifier output 10 is conducted to the divide-by-N logic 18 which is assumed to be in the divide-by-one mode. In the divide-by-one mode, this logic will produce a single output at output 38 for each input pulse communicated to input 19. Consequently, the atrial sense amplifier signal will initiate the A-V delay counter 14 by transmitting a trigger pulse to the trigger input 16 of the counter through the divide-by logic 18 when the divide-by logic is in the divide-by-one mode. The A-V counter 14 counts clock pulses and produces an output at output 20 after a preset time unless the counter is reset to zero by a logic level input on reset input 34. In the example, if the detected atrial event is not followed by a ventricular depolarization within the delay period of the A-V counter 14, then a counter overflow signal from output 20 will be conducted to trigger input 24 at the output control logic 22 resulting in a logic level output at output 26 which triggers the output buffer 28 through its trigger input 30 to produce a ventricular stimulating pulse. In this fashion, a detected atrial event has resulted in the issuance of a ventricular stimulating pulse.

Turning to the ventricular inhibited or VVI mode, it is important to recall that ventricular stimulating pulses are communicated to the ventricle only in the absence of sensed ventricular depolarizations below a preset demand rate. In this mode, the atrial sense amplifier 12, the divide-by logic 18 and the A-V delay counter 14 may be ignored. In operation a ventricular depolarization is coupled to the ventricular sense amplifier 32 through conductor 7. The ventricular sense amplifier produces a logic level output at output 36 in response to a detected ventricular event. This signal is coupled to the low rate counter through reset input 44 which resets the low rate counter 42 to a preset number. The low rate counter then counts clock pulses and will produce an overflow on output 50 if the counter is not again reset within a preset time interval. If no ventricular activity is detected within the defined time limit, then output from output 50 will trigger the output control logic 22 through its trigger input 52 and result in an output pulse from output 26 which triggers the output buffer through its trigger input 30 resulting in a stimulus output delivered to the ventricle from output 29 through conductor 7.

As previously described, switching from the VDD mode to the VVI mode is automatically accomplished by detection of an intrinsic atrial rate below the hysteresis rate corresponding to point C of FIG. 1. Automatic return from the VVI mode to the VDD mode is accomplished by detection of an intrinsic atrial rate above the lower rate indicated by point B of FIG. 1.

When the pacer is operating in the VDD mode, a hysteresis rate value is transferred through the multiplexer to the low rate counter which, in this example, corresponds to a thirty-beat-per-minute rate. If the detected cardiac rate drops below this value, then the lower rate counter will overflow. This initiates an output pulse through output logic 26 and also sets the hysteresis control flip-flop to a logic 1 value. The logic 1 of the hysteresis control flip-flop is communicated to the multiplexer which loads the lower rate value into the lower rate counter and additionally sets the divide-by-N logic to the divide-by-two configuration. At this point the mode switch from VVD to VVI is complete, and the lower rate value loaded in the lower rate counter will correspond to a shorter escape interval corresponding to a 70 bpm demand pacing rate. The first ventricular stimulating output pulse resets the divide-by-N logic to the zero count condition. In this condition two input pulses to the divide-by-N logic input terminal are required to produce a single output pulse at the output terminal. During operation in the VVI mode at atrial rates below 70 beats per minute, the divide-by-N logic will never reach the count 2 condition. Consequently, as long as the atrial rate is below the preset lower rate, the low rate counter will overflow producing ventricular-stimulating pulses in accordance with the VVI demand function. If, however, the atrial rate exceeds the lower rate setting, then the divide-by-N logic will reach a count of two, producing a reset pulse at hysteresis control flip-flop, forcing its output to a logic zero condition. A logic zero at the hysteresis control flip-flop output permits the hysteresis rate value to be transferred through the multiplexer to the low rate counter. Additionally, the low output of the hysteresis control will reset the divide-by-N logic to the divide-by-one configuration, thus returning the pacer to the VVD pacing mode.

The preceding description of the VVI and VDD modes has not involved a discussion of the refractory and upper rate counter 56 as well as the rate limit logic 54. Although these elements are not necessary for the understanding of the invention, they are required in a commercially viable pacer. The purpose of rate limit logic 54 is to prevent component failure within the pacemaker from resulting in a pacer-induced tachycardia as more fully described in U.S. Pat. No. 3,391,697 "Runaway Inhibited Pacemaker" to Wilson Greatbatch. The digital implementation suggested by FIG. 2 involves a counter which is reset in synchrony with the low rate counter 42 and which times out after a suitable delay period. The overflow, or TIME OUT signal, from output 60 is communicated to the enable input 62 of output control logic 22. The output control logic will not respond to a trigger input on either of its trigger inputs 24 or 52 unless an appropriate logic level is present on an enable input 61 or 62. In operation, the rate limit logic provides such an ENABLE signal on enable input 62 after a 300 millisecond delay corresponding to a runaway limit of approximately 200 bpm.

Although the invention is described in the context of a VDD pacemaker, it could as well be implemented in other atrial and ventricular pacemakers, including the DVI, or A-V sequential pacemaker and the DDD or fully automatic atrial and ventricular pace and sense pacemakers (the symbols VDD, DVI DDD following the nomenclature adopted in the Inter-Society Commission for Heart Disease Resource Code published by the *Americal Journal of Cardiology,* 34, 487, 1974).

We claim:

1. A pacer for producing ventricular stimulating pulses at rates between an upper atrial synchronous rate (A) and a lower hysteresis rate (C) in an atrial synchronous mode; when the detected atrial rate lies between said upper atrial synchronous rate and said hysteresis rate, and for producing ventricular stimulating pulses at a ventricular inhibited rate (DB) in a ventricular inhibited mode when the detected atrial rate falls below said hysteresis rate (C) and wherein said pacer returns to said atrial synchronous mode when the detected atrial rate exceeds a preselected atrial rate (B) which is higher than said hysteresis rate (C) but lower than said upper atrial synchronous rate (A); said pacer comprising:

ventricular pulse generator means for producing ventricular stimulating pulses, operated in response to a ventricular pace signal;

first sensing means for detecting atrial depolarizations and for producing an atrial sensed signal;

second sensing means for detecting ventricular depolarizations and for producing ventricular sensed signals;

ventricular escape interval timing means defining a ventricular escape interval responsively coupled to said ventricular sensed signal for producing a ventricular pace signal if no atrial or ventricular sensed signal is produced within said ventricular escape interval;

atrio-ventricular escape interval timing means defining an atrio-ventricular escape interval said interval being initiated in response to said atrial sensed signal for producing a ventricular pace signal if no ventricular sensed signal is produced within said atrio-ventricular escape interval;

atrial rate measuring means for preventing said atrio-ventricular escape interval timing means from produced ventricular pace signals if the measured atrial rate is below a hysteresis rate (C) thus preventing atrial synchronized pacing at low atrial rates.

2. The pacer of claim 1 wherein said atrial rate measuring means further comprises means for permitting said ventricular escape interval means to produce a ventricular pace signal if no ventricular sensed signal is produced within a ventricular escape interval.

3. The pacer of claim 1 or claim 2 further including:

atrial pulse generator means for generating stimulating pulses adapted to be applied to the atrium in response to an atrial pace signal; and wherein said ventricular escape interval timing means further comprises means for producing an atrial pace signal prior to producing a ventricular pace signal if no ventricular or atrial sensed signal is produced within a ventricular escape interval.

4. A mode adaptive pacer for the therapeutic stimulation of the ventricles of the heart comprising:

a ventricular pulse generator for producing a ventricular stimulus in response to a ventricular pace signal;

a programmable lower rate counter defining a ventricular escape interval, and for producing a ventricular pace signal at the expiration of the ventricular escape interval;

a programmable A-V delay counter defining an atrioventricular delay interval, and for producing a ventricular pace signal at the expiration of the A-V delay interval;

a ventricular sense amplifier producing a ventricular escape interval reset signal in response to ventricular depolarizations;

an atrial sense amplifier responsive to atrial depolarizations for initiating said A-V delay counter; and divide-by-N logic interposed and coupled between said atrial sense amplifier and said A-V delay counter, wherein N is set equal to 1 for atrial synchronous pacing and wherein N is set equal to 2 in response to the expiration of said ventricular escape interval.

* * * * *